(12) United States Patent
Uria

(10) Patent No.: US 6,770,289 B2
(45) Date of Patent: Aug. 3, 2004

(54) LIQUID PHARMACEUTICAL COMPOSITION FOR TREATING BONE DISEASES

(75) Inventor: Guadalupe Martinez Uria, Buenos Aires (AR)

(73) Assignee: Riderway Corporation, Panama (PA)

(*) Notice: Subject to any disclaimer, the term of this patent is extended or adjusted under 35 U.S.C. 154(b) by 162 days.

(21) Appl. No.: 10/066,008

(22) Filed: Feb. 1, 2002

(65) Prior Publication Data

US 2002/0142997 A1 Oct. 3, 2002

Related U.S. Application Data

(60) Provisional application No. 60/265,827, filed on Feb. 1, 2001.

(51) Int. Cl.⁷ .............................. A61F 2/02; A61F 2/28
(52) U.S. Cl. ..................... 424/423; 523/114; 523/115
(58) Field of Search ..................... 424/423; 523/114, 523/115

(56) References Cited

U.S. PATENT DOCUMENTS 6,143,326 A   11/2000   Mockel et al.

FOREIGN PATENT DOCUMENTS

EP   1 228 761 A2 *   8/2002

OTHER PUBLICATIONS

Eastell, R., "Treatment of Postmenopausal Osteoporosis", Journal of Medicine, 338: 1998, pp. 736–746.

Lane, J.M., "Osteoporosis–Medical Prevention and Treatment", Spine, 22: 1997, pp. 32–37.

* cited by examiner

Primary Examiner—Carlos A. Azpuru
(74) Attorney, Agent, or Firm—Darby & Darby

(57) ABSTRACT

The invention provides a liquid pharmaceutical composition and methods for use in the treating of bone diseases, the composition being an aqueous solution comprising 0.05% to 35% by weight of ibandronaic acid or salts thereof; 0.1% to 5% by weight of a pH regulating agent; 1% to 15% by weight of a co-solvent; 0.005% to 0.5% by weight of a conserving agent; 1% to 90% by weight of a deionized water; and excipients and pharmaceutically acceptable stabilizers, wherein the composition has a pH of about 2 to 7. The composition is formulated for sublingual administration and enteric administration.

16 Claims, No Drawings

LIQUID PHARMACEUTICAL COMPOSITION FOR TREATING BONE DISEASES

The application claims benefit of 60/265,827 filed Feb. 1, 2001.

BACKGROUND OF THE INVENTION

1. Field of the Invention

The present invention relates to the medical field and more particularly to pharmaceutical compositions containing ibandronaic acids or salts thereof and method for treating osseous diseases and disorders in the calcium metabolism. The invention also provides methods for obtaining the compositions.

2. Description of the Prior Art

An increasing number of individuals affected by diseases related to the loss of osseous mass has been a concern in the last years. Many of these affections are related to endocrine pathologies or cancer, to treatments based in the use of pharmaceuticals and menopause. In this latter case the process is characterized by a high osseous disorder affecting to the 25% of post-menopause women. When forms not so severe like the osteopenia are considered, the incidence is considerably increased. All these osseous affections could be encircled within the osseous diseases, particularly within those diseases having disorders in the calcium metabolism.

During the last years it has been progressed in the knowledge, diagnostic and treating of the senile involutional osteoporosis which, differing from the above mentioned affections, it is characterized by a little osseous renewal thus causing the traditional therapeutic focusing to be modified.

At present there are more reviewing over the osteoporosis question, its prevention and treatment in the different clinic situations (Eastell, R. New England Journal of Medicine, 338: 736–746, 1998 and Lane, J. M. "Osteoporosis-Medical Prevention and Treatment". Spine, 22: 32–37, 1997).

It is considered that supplementing calcium is a necessary condition for treating osteopenia/osteoporosis, but this is not enough for obtaining the desired results. Administering calcium and vitamin D is the first treatment option in post-menopause women.

Other types of treatments include: hormonal replacing therapy, partial estrogenic agonists (SERM), agents for stimulating the osseous synthesis and agents for inhibiting the osseous resorption. Within the group including the agents for inhibiting the osseous resorption, the bisphosphonates are in a relevant position.

Bisphosphonates are analogous to pyrophosphate, and include a phosphorous-carbon-phosphorous column in its chemical composition and the bisphosphonates are bonded to the surface of hydroxyapatite crystals, particularly in the sites of the bone for active re-modeling.

There are several bisphosphonate generations. Within a first generation the etidronate is compressed and it is employed in prevention and treating methods by administering doses of 400 mg in three month cycles, together with supplementing of about 800 to about 1250 mg/day of calcium during a break period. The alendronate is another medicament that has shown effectiveness when orally administered together with calcium and, eventually, with vitamin D. This compound is useful either in prevention as well as in treating procedures, remarkably increasing the mineral osseous density at a long term, and reducing the incidence of bone fractures in patients with osteoporosis. For prevention purposes the dose is 5 mg/day administered in fasting. For treatment purposes, 10 mg/day fasting doses are administered. However, the alendronate is related to many side effects, particularly irritations in the esophagus and gastritis. For preventing this gastric irritations and oesophagitis, this pharmaceutical product must be administered in fasting with the patient in a stand up position and by drinking a lot of water.

The above mentioned drawbacks make this product to be very cumbersome for administration, particularly when the patient must be subject to a treatment for general osteoporosis and, more particularly, when the patient is undergoing a treatment of involutional osteoporosis because the same is found in elderly individuals. Due to this inconveniences, the product must be administered in doses below 10 mg. Other bisphosphonates are: pamidonate, risedronate, zolendronate and ibandronate.

The modern non halogenated bisphosphonates (amino-bisphosphonates) actuate via several mechanisms such as, competing for the osteoplastic action site at the level of free osseous surfaces, reducing the osteoplastic recruiting and incrementing the apoptosis of osteoplasts.

Ibandronate is employed in the treatment of osseous metastasis and neoplastic hypercalcaemias, in the form of injectable solutions. The ibandronate is administered via intravenous application at a rate of about 1 mg to about 5 mg each 1 to 6 months, but it maybe also orally administered at doses of 0.5 mg to 5 mg per tablet according to the particular indications.

U.S. Pat. No. 6,143,326 to Mockel et al. discloses a method of treating a bone disease by administering to the patient a pharmaceutical formulation comprising a tablet core containing about 0.1 mg to 100 mg of ibandronate. It is well known in the art that all the treatments by early administering ibandronate are specially complex and cumbersome because of the poor gastric absorption as well as of the side effects produced by the ibandronate. Among these effects is to be remarked the esophageal irritation. These ibandronate compounds in solid tablets to be orally administered must be ingested under certain conditions to diminish the irritating effects.

It would be therefore very desired in the art to have a new form of a pharmaceutical compound containing ibandronate to be administered to the patients in need thereof without the above mentioned side effects and drawbacks.

SUMMARY OF THE INVENTION

It is therefore an object of the invention to provide a pharmaceutical composition containing ibandronaic acid or the salts thereof which are manufactured in none parenteral pharmaceutical forms which represents a significant therapeutic development and which leads to an easy administration thereof without the side effects produced by typical pharmaceutical forms such as the gastric intolerance, the invented composition providing a rapid absorption with excellent results in connection to the osseous synthesis and re-absorption biochemical markers.

It is still another object of the present invention to provide a liquid pharmaceutical composition for use in the treating of bone diseases, the composition being an aqueous solution comprising about 0.05% to about 35% by weight of ibandronaic acid or salts thereof; about 0.1% to about 5% by weight of a pH regulating agent; about 1% to about 15% by weight of a co-solvent; about 0.005% to about 1.5% by weight of a conserving agent; about 1% to about 90% by weight of a de-ionized water; and excipients and pharmaceutically acceptable stabilizers, wherein the composition has a pH of about 2 to 7. The pH regulating agent being acetates, phosphates, citrates, ascorbates, or bases and acids thereof, with the citric acid or the sodium salt thereof being the preferred ones. The co-solvent being glycol, glycerol or mixtures of same, with the preferred co-solvent being propylene glycol, and the conserving agent is nipagin or nipasol.

It is even another object of the present invention to provide a method of making the immediately above disclosed composition, comprising the steps of:

a) dissolving the pH regulating agent in de-ionized water to form a solution;

b) adding the ibandronate to the solution of step a) and agitating the solution until obtaining a complete dissolution;

c) adding the co-solvent while maintaining said agitation;

d) adding de-ionized water for bringing the solution to a final weight and sterilizing the solution by passing it through 0.22 μm filter. If necessary, an step of measuring the pH of the solution and bringing the pH to about 2 to about 3 is carried out before step d).

It is a further object of the present invention to provide a liquid pharmaceutical composition for use in the treating of bone diseases, the composition being an aqueous solution comprising, per each 100 g of solution, about 2 g to about 35 g of sodium ibandronate; about 0.8 g to about 1.5 g of monohydrate citric acid; about 15 g to about 25 g of propylene glycol, and water and pharmaceutically acceptable excipients, wherein the final pH of the composition is about 2 to about 3.

It is even another object of the present invention to provide a method of making the immediately above disclosed composition, comprising the steps of:

a) dissolving the citric acid in de-ionized water to form a solution;

b) adding the ibandronate to the solution of step a) and agitating the solution until obtaining a complete dissolution;

c) adding the propylene glycol to the solution while maintaining said agitation;

d) adding de-ionized water for bring the solution to a final weight and sterilizing the solution by passing it through 0.22 μm filter. If necessary, an step of measuring the pH of the solution and bringing the pH to about 2 to about 3 may be carried out before step d).

It is even another object of the present invention to provide liquid pharmaceutical composition for use in the treating of bone diseases, the composition being an aqueous solution comprising, per each 100 g of solution, about 0.15 g to about 0.30 g of sodium ibandronate; about 0.39 to about 0.7 g of sodium citrate; about 6.5 g to about 7.5 g of propylene glycol, and about 0.001 g to about 0.1 g of nipagin; about 0.002 g to about 0.5 g of nipasol; about 1 g to about 2 g of sorbitol; and water and pharmaceutically acceptable excipients, wherein the final pH of the composition is about 6.5 to about 7.

It is even another object of the present invention to provide a method of making the immediately above disclosed composition, comprising the steps of:

a) dissolving the nipagin and nipasol in an amount of de-ionized water equivalent to the 50% of the final volume of the composition, at a temperature of about 70° C. to about 85° C. and under agitation;

b) cooling down the solution to 35° C. and adding the sorbitol and the sodium citrate while agitating up to the complete dissolution;

c) adding the propylene glycol under agitation; and d) adding the sodium ibandronate and agitating up to a complete dissolution. If necessary, a step of bringing the pH of the solution to about 6.5 to about 7 may be carried out after step d).

It is even another object of the present invention to provide a method of treating a bone disease in a patient in need thereof, the method comprising administering to the patient about 2.5 mg/day to about 10 mg/day of ibandronaic acid or salts thereof in any of the above mentioned compositions, wherein the administration of the composition may be via sublingual or via intranasal.

The above and other objects, features and advantages of this invention will be better understood when taken in connection with the accompanying drawings and description.

DETAILED DESCRIPTION OF THE INVENTION

A comparative clinic test has been carried out with 9 patients affected by menopause during a minimum of 18 months and a maximum of 37 months. The 49 to 53 years old patients were subdivided into three aleatory groups. Group 1 has been treated with an enteric composition of the invention containing ibandronate, which composition has been obtained according to the following Example 2 and the treatment carried out according to the scheme disclosed in Example 3. Group 2 has been treated with an enteric sublingual composition containing ibandronate according to the invention, which composition has been obtained according to Example 1 and the treatment carried out according to the scheme disclosed in Example 3. Group 3 has been treated with solid oral formulations containing ibandronate of commercial use according to a treatment scheme disclosed in Example 3.

The evaluation of the action profiles corresponding to the three ibandronate compounds employed in the clinic tests has been carried out on the basis of the evolution of biochemical markers of osseous re-absorption (CT) and osseous synthesis (FAO). A 10% variation for the intra-test and a 25% variation for the method, have been considered for these tests. Reductions of about 50% or more in the CT circulating levels have been considered as remarkable while changes below those percentages have been considered irrelevant.

The results of the comparative clinic test carried out according to what is disclosed below, in Example 3, showed that the calcaemia values in the patients were within the normal rates and without significant variations along all the clinic test. The calciuria values also were within the normal rates, but they had a significant increasing at the two month from the beginning of the treatment with calcium.

The following Tables 1, 2 and 3 show the individual values and the average values±DS for products degrading the C-terminal telopeptides of collagen type I (CT), osteospecific alkaline phosphatase (FAO) and PTH corresponding to the patients treated with the inventive enteric solution, the inventive sublingual solution and the traditional tablets.

TABLE 1

Evaluation of CT, FAO and PTH employing the enteric solution of the invention

|  | Patient IS | Patient MS | Patient FL | Mean | DS |
|---|---|---|---|---|---|
| CT (pM) | | | | | |
| B1 | 8096 | 8781 | 1485 | 6120.7 | 4029.2 |
| B2 | 6472 | 8463 | 1123 | 5352.7 | 3795.9 |
| V7 | 5209 | 9115 | 1063 | 5129.0 | 4026.6 |
| V14 | 4405 | 6154 | 893 | 3817.3 | 2679.3 |
| V21 | 3833 | 5717 | 456 | 3335.3 | 2665.6 |
| V28 | 3075 | 5385 | 238 | 2899.3 | 2577.9 |
| V45 | 2905 | 5222 | 220 | 2782.3 | 2503.3 |
| V60 | 2902 | 4478 | 164 | 2514.7 | 2182.9 |
| V90 | 3075 | 4455 | 210 | 2580.0 | 2165.4 |
| FAO (U/1) | | | | | |
| B1 | 61 | 37 | 22 | 40.0 | 19.7 |
| B2 | 58 | 36 | 35 | 43.0 | 13.0 |
| V7 | 59 | 34 | 33 | 42.0 | 14.7 |
| V14 | 59 | 33 | 34 | 42.0 | 14.7 |
| V21 | 55 | 37 | 33 | 41.7 | 11.7 |
| V28 | 51 | 30 | 35 | 38.7 | 10.9 |
| V45 | 58 | 32 | 33 | 41.0 | 14.7 |
| V60 | 54 | 32 | 36 | 40.7 | 11.7 |
| V90 | 46 | 32 | 34 | 37.3 | 7.6 |
| PTH (pg/ml) | | | | | |
| B1 | 36 | 19 | 47 | 34.0 | 14.1 |
| B2 | 22 | 16 | 37 | 25.0 | 10.8 |
| V90 | 20 | 15 | 23 | 19.3 | 4.0 |

TABLE 2

Evaluation of CT, FAO and PTH employing the sublingual solution of the invention

|  | Pat AC | Pat AB | Pat AE | Mean | DS |
|---|---|---|---|---|---|
| C-telo. PM | | | | | |
| B1 | 3152 | 4776 | 3585 | 3837.7 | 840.9 |
| B2 | 2804 | 4059 | 3186 | 3349.6 | 643.3 |
| V7 | 238 | 2500 | 800 | 1179.3 | 1177.7 |
| V14 | 100 | 1856 | 793 | 916.3 | 884.4 |
| V21 | 100 | 1236 | 703 | 679.7 | 568.4 |
| V28 | 100 | 385 | 100 | 195.0 | 164.5 |
| V45 | 100 | 528 | 100 | 242.7 | 247.1 |
| V60 | 120 | 284 | 100 | 168.0 | 100.9 |
| V90 | 100 | 192 | 100 | 130.7 | 53.1 |
| FAO U/I | | | | | |
| B1 | 25 | 29 | 42 | 32.0 | 8.9 |
| B2 | 25 | 22 | 35 | 27.3 | 6.8 |
| V7 | 28 | 23 | 37 | 29.3 | 7.1 |
| V14 | 24 | 23 | 34 | 27.0 | 6.1 |
| V21 | 27 | 21 | 30 | 26.0 | 4.6 |
| V28 | 27 | 20 | 30 | 25.7 | 5.1 |
| V45 | 23 | 17 | 29 | 23.0 | 6.0 |
| V60 | 22 | 18 | 27 | 22.3 | 4.5 |
| V90 | 21 | 17 | 27 | 21.7 | 5.0 |
| PTH pg/ml | | | | | |
| B1 | 61 | 23 | 33 | 39.0 | 19.7 |
| B2 | 47 | 19 | 33 | 33.0 | 14.0 |
| V7 | | | | | |
| V14 | | | | | |
| V21 | | | | | |
| V28 | | | | | |
| V45 | | | | | |
| V60 | | | | | |
| V90 | 31 | 18 | 20 | 28.0 | 11.3 |

TABLE 3

Evaluation of CT, FAO and PTH employing the traditional tablets

|  | Pat ZU | Pat VS | Pat DF | Mean | DS |
|---|---|---|---|---|---|
| C-telo. PM | | | | | |
| B1 | 6097 | 4678 | 2487 | 4420.7 | 1818.7 |
| B2 | 6032 | 4555 | 2423 | 5352.7 | 3795.9 |
| V7 | 5670 | 4322 | 2211 | 4067.7 | 1743.5 |
| V14 | 4010 | 4123 | 988 | 3040.3 | 1778.3 |
| V21 | 3233 | 3456 | 776 | 2488.3 | 1487.1 |
| V28 | 2944 | 3233 | 1120 | 2432.3 | 1145.7 |
| V45 | 2789 | 3144 | 879 | 2270.7 | 1218.2 |
| V60 | 2897 | 2980 | 928 | 2268.3 | 1161.5 |
| V90 | 2321 | 2878 | 956 | 2051.7 | 988.9 |
| FAO U/I | | | | | |
| B1 | 51 | 39 | 30 | 40.0 | 10.5 |
| B2 | 48 | 39 | 29 | 38.7 | 9.5 |
| V7 | 50 | 35 | 23 | 36.0 | 13.5 |
| V14 | 49 | 37 | 24 | 36.7 | 12.5 |
| V21 | 46 | 35 | 22 | 34.3 | 12.1 |
| V28 | 42 | 32 | 21 | 31.7 | 10.5 |
| V45 | 47 | 30 | 23 | 33.3 | 12.3 |
| V60 | 43 | 27 | 24 | 31.3 | 10.2 |
| V90 | 44 | 28 | 21 | 31.0 | 11.8 |
| PTH pg/ml | | | | | |
| B1 | 32 | 29 | 47 | 36.0 | 9.6 |
| B2 | 29 | 23 | 46 | 32.7 | 11.9 |
| V7 | | | | | |
| V14 | | | | | |
| V21 | | | | | |
| V28 | | | | | |
| V45 | | | | | |
| V60 | | | | | |
| V90 | 25 | 25 | 43 | 31.0 | 10.3 |

As it may be seen from Table 1 two of the patients treated with the enteric composition of ibandronate, had very high starting levels of CT and all showed a definite drop of the circulating levels of this marker, with the minimum levels being reached at the 60 to 90 days of treatment. This expression in the osseous re-absorption reduction did not reach, in average, the 50% of the starting values, however, the individual patients IS and FL had drops above the 50% of the starting value.

The starting circulating levels of FAO were high in two of the patients, without significant variations being detected with the treatment. The three patients of this group showed normal PTH starting values, which values dropped after the patients were administered with a calcium supplement.

Upon analyzing the results in the patients treated with the sublingual drops of the invention (see Table 2) it may be concluded that the CT starting basal levels were high and that these levels dramatically dropped between days 7 and 14 after the beginning of the treatment. The reduction of this osseous re-absorption marker reached its minimum level on day 28 from the treatment, and it has been maintained without significant changes subsequently up to the end of the clinic test.

In connection to the FAO levels, as expression of osseous synthesis, the basal values were higher in two of the three tested patients, while a light but systematic decreasing between days 45 and 60 of the treatment has been observed.

The PTH was initially high in the patients and decreased after the initial administration of calcium.

Two of the patients treated with tablets of ibandronate of traditional use (Table 3) showed higher starting CT levels and all patients showed a drop of the circulating levels of this marker, reaching minimum values between the 60 and 90 days of the treatment. This expression of osseous re-absorption decreasing did not reach the 50% of the initial values in one of the patients while the other two patients showed drops above 50%.

It was also observed that the FAO levels were initially high, without significant variations being observed with the treatment, except a decreasing thereof at the end of the period of testing.

In the three patients of this group, the initial PTH values were normal and the same decreased after ingesting a calcium supplement.

No significant variation in the complement of the examinations carried out in the three groups of patients under testing were observed.

Analysis of Pre and Post Results from Calcium Treatment

The initial basal levels of CT were high in most of patients as an expression of osseous re-absorption increased as a result of the post-menopausic osteoporosis that were affecting the patients. The levels after supplementing the patients with calcium and before treatments with ibandronate in its different formulations did not remarkably differ from the basal values in the three groups under testing. Therefore, it may be said that the treatment with calcium, which can have influence on the PTH reduction (as it is clear from the observed circulating levels of this hormone) would not have modified per se the levels corresponding to the osseous anti-re-absorptive activity.

In connection to the FAO basal levels, seven of the nine patients had high levels, which levels did not changed after the initial period of treatment with calcium.

Analysis of the Post Results of Treatments with Ibandronate in its Three Formulations When the values of the biochemical markers have been compared after the several treatments had been carried out (enteric solution, sublingual drops and traditional tablets), the enteric solution and the tablets showed a similar effect as to the CT values. Both formulations produced a drop of about 50% or more in the CT values with a very few influence over the FAO values. The effect over the CT was shown after day 28 of the treatment.

On the other hand, sublingual drops had a much more intense effect on the CT, with a decrease above a 90%, and said effect was early observed, more particularly very early, at day 7 of treatment, with the effect being maintained at a low level up to the end of the treatment. The effects on the FAO were clear as from day 45.

This results show that the activity of the sublingual drops are clearly different from the activity of the tablets because the drops generate much higher decreasing of the osseous reabsorption parameter, with this decreasing appearing earlier and being higher than the decreasing observed with the administration of ibandronate enteric solution and the tablets. The inventive composition in the form of sublingual drops provides an important decreasing of the osseous turn over, without esophageal path and therefore without side effects appearing in the patients. In addition, differing from the intravenous formulations, the drops are administered through an easier way particularly accepted by elder patients.

The liquid composition containing ibandronate according to the invention, for sublingual administration, shows a better absorption because the active substance is absorbed as ibandronaic acid and not as a salt. The active substance is found as acid because of the composition pH which is between 2 and 3. In addition, the sublingual administration provides a higher bio-availability and a shorter maximum period of time of concentration, thus avoiding the first step effect.

As it is shown in the examples, the method of obtaining the inventive sublingual composition is simpler as compared to the obtention of other solid or injectable formulations, the method providing an improvement as to the productions or yields and costs economy.

It would be apparent for any expert in the art that the invented formulation may include any pH regulating agent such as citric acid, sodium citrate, phosphoric acid and phosphates. The co-solvent may be propylene-glycol, polyethylene-glycol, hydroxi-stearic acid glycerides. Any organolepetic adjuvant may be employed such as sorbitol, essences, sweeteners. Any conserving agent may also be employed such as nipagin, nipasol, boric acid, salts, ammonium-quaternaries. In addition, any pharmacologically acceptable excipient may also be used, all the above agents and components being within the scope of the present invention.

The inventive compositions may be employed for treating the following diseases or disorders related to calcium metabolism: a) primary and secondary osteoporosis (for example, post-menopausic, involutive senile, diseases due to corticoids, due to renal insufficiency in patients subject to transplant operations); b) prevention of osseous metastasis in several neoplastics; c) Paget's diseases; d) treatment of osseoltic metastasis in several carcinomas; e) multiple-mieloma. The invented solution may be administered in doses between 2.5 mg per day and 5 mg per day for an extended treatment of osteoporosis. For treating the Paget's disease the patients may be administered with between 2.5 mg per day to 10 mg per day of the composition for a long period of time. The multiple-mieloma can be treated with doses between 2.5 mg per day to 10 mg per day for a long period of time. For prevention and/or treating of osseoltic metastasis it is recommended to administer doses between 2.5 mg per day to 10 mg per day during long periods of time. Finally, it is also possible to design other treatment schemes but may be non continuous treatments.

The following examples better illustrate the various embodiments now contemplated for practicing the invention but they should not be construed to limit the invention.

EXAMPLE 1

Preparation of the Inventive Composition for Sublingual Administration

For obtaining 100 g of the composition 1200 mg of monohydrate citric acid has been dissolved in an amount of deionized water equivalent to 22% of the final weight of the formulation. 2810 mg of $H_2O$ sodium ibandronate were subsequently added to the solution and agitation was applied up to reaching a complete dissolution.

20 mg of propilenglycol were added while maintaining the agitation. Subsequently the pH was measured and it was adjusted to 2.4. Then, deionized water was added in an amount enough to bring the formulation to 100 g.

Finally, the solution was filtered by using $0.22\mu$ filters.

EXAMPLE 2

Preparation of the Inventive Composition for Enteric Administration

For obtaining 100 g of the composition 70 mg of nipagin and 30 mg of nipasol were dissolved in an amount of deionized water equivalent to 50% of the final weight of the formulation under agitation and at a temperature of 75° C. The solution was cooled down up to reaching a temperature of 35° C. and 1666.7 mg of sorbitol and 500 mg of sodium citrate were added under agitation H₂O sodium ibandronate were subsequently added to the up to obtaining a complete dissolution.

8.33 mg of propilenglycol were added while maintaining the agitation. Subsequently the pH was measured and it was adjusted to 7.0. Then, deionized water was added in an amount enough to bring the formulation to 100 g.

EXAMPLE 3

Comparative Clinic Tests

A comparative clinic test was carried out with 9 patients affected by menopause for a minimum period of 18 months and a maximum period of 37 months. The patients were between 49 and 53 years old patients. The daily ingestion of elemental calcium was between about 570 mg and about 680 mg. All the patients had a positive osteoporosis diagnosis evaluated by osseous densimetry with a Body Mass Index (BMI) rate between 19 and 25. The osteoporosis diagnosis was defined according to WHO's Report 843.

The patients already affected by the following diseases were excluded from the test: phosphocalcic metabolism diseases other than osteoporosis, hyperparathyroidism, hypoparathyroidism, osteomalacia, renal recidivismal lithiasis, hydiopatic hypercalciuria, hypercorticalism, hyperthyroidism, hypergonadism antecedents in reproductive age, hyperprolactinemia, renal insufficiency, renal osteodystrophy, neoplastics from any origin, malabsorption syndrome, rheumatoid arthritis, ankylosed spondylitis, multiple myeloma, chronic hematologic diseases, porphyria, melitose diabetes type I or II, alcoholism and other addictions, chronic treatments with corticoids, thyroid hormone therapy in inhibiting doses for more than 2 years, anticonvulsants, heparin, non heparinic anticoagulants, anti-ulceratives and alkaline,dementia, cognitive disorders, gastroduodenal ulcer, oesophagitis, gastritis, hepatic insufficiency, decompensated neuropathies and/or cardiopathies.

General laboratory controls, osseous densimetry (DMO) and feeding anamnesis were applnied to each patient. The laboratory control tests were carried out from serum and plasma conserved at −20° C. up to the use thereof.

As from the beginning of the tests the patients were administered with a daily supplement of 1000 mg of elemental calcium in a calcium citrate suspension (Citramar™ Suspension containing 100 mg of elemental calcium/ml).

At the 60 days from the beginning of the treatment with a daily supplement of calcium blood samples were taken from the patients and the samples were separated in three groups:

Group 1). three patients that were administered with 2.5 mg/day of ibandronate in enteric form (composition of the invention in enteric solution).

Group 2). three patients that were administered with 2.5 mg/day of ibandronate in sublingual form (composition of the invention in sublingual drops).

Group 3). three patients that were administered with 2.5 mg/day of ibandronate in traditional tablet form.

During the 90 days of treatment blood samples were taken on days 7, 14, 21, 28, 45, 60 and 90, and the serum and plasma was conserved at −200° C. up to the use thereof. The samples were processed as follows:

Blood count and hepatogram.

Total calcium circulating levels, in mg/100 ml. Normal values 8.6 to 10.2 mg/100 ml.

Urinary calcium excreted per day, in mg/24 hr. Normal values 100 to 350 mg/day, employing Equipment BM/Hitachi 704/911.

Intact PTH circulating levels, in pg/,l. Normal values 9 to 55 (intra-test variation 3.5% —inter-test variation 4.6%), employing an equipment DSL-800 commercially available from Diagnostic System Laboratories, Texas, U.S.A.

Serum levels of osteospecific alkaline phosphatase, in U/l. Normal values 11.6 to 29.6 U/l (intra-test variation 3.9% — inter-test variation 7.6%), employing an equipment Alkphase-B commercially available from Biosystems Inc., California U.S.A.

Serum levels of the product degrading the C-telopeptide terminal of collagen type I, in pM. Normal values 1200 to 3410 pM, (intra-test variation 6.1% —inter-test variation 7.1%), employing an equipment FERUM Cross Laps commercially available from Osteometer Bio Tech, Denmark.

While preferred embodiments of the present invention have been illustrated and described, it will be obvious to those skilled in the art that various changes and modifications may be made therein without departing from the scope of the invention as defined in the appended claims.

I claim:

1. A liquid pharmaceutical composition for use in the treating of bone diseases, the composition being an aqueous solution comprising:

about 0.05% to about 35% by weight of ibandronaic acid or salts thereof;

about 0.1% to about 5% by weight of a pH regulating agent;

about 1% to about 15% by weight of a co-solvent;

about 0.005% to about 1.5% by weight of a conserving agent;

about 1% to about 90% by weight of a deionized water; and at least one excipient or pharmaceutically acceptable stabilizers, wherein the composition has a pH of about 2 to 7.

2. The composition of claim 1, wherein the pH regulating agent is selected from the group comprising acetates, phosphates, citrates, ascorbates, and bases or acids thereof.

3. The composition of claim 1, wherein the pH regulating agent is citric acid or the sodium salt thereof.

4. The composition of claim 1, wherein the co-solvent is selected from the group comprising glycol, glycerol and mixtures of same.

5. The composition of claim 1, wherein the co-solvent is propylene glycol.

6. The composition of claim 1, wherein the conserving agent is selected from the group comprising nipagin and nipasol.

7. The composition of claim 1, wherein each 100 g of the aqueous solution comprises:

about 2 g to about 35 g of sodium ibandronate;

about 0.8 g to about 1.5 g of monohydrate citric acid;

about 15 g to about 25 g of propylene glycol, and water and pharmaceutically acceptable excipients, wherein the final pH of the composition is about 2 to about 3.

8. The composition of claim 1, wherein each 100 g of the aqueous solution comprises:
   about 0.15 g to about 0.30 g of sodium ibandronate;
   about 0.3 g to about 0.7 g of sodium citrate;
   about 6.5 g to about 7.5 g of propylene glycol, and about 0.001 g to about 0.1 g of nipagin;
   about 0.002 g to about 0.5 g of nipasol;
   about 1 g to about 2 g of sorbitol; and
   water and pharmaceutically acceptable excipients, wherein the final pH of the composition is about 6.5 to about 7.

9. A method of making the composition of claim 7, comprising the following steps:
   a) dissolving the citric acid in deionized water to form a solution;
   b) adding the ibandronate to the solution of step a) and agitating the solution until obtaining a complete dissolution;
   c) adding the propylene glycol to the solution while maintaining said agitation;
   d) adding deionized water for bring the solution to a final weight and sterilizing the solution by passing it through 0.22 μm filter.

10. The method of claim 9, further comprising, before step d), the step of measuring the pH of the solution and bringing the pH to about 2 to about 3.

11. A method of making the composition of claim 8, comprising the following steps:
   a) dissolving the nipagin and nipasol in an amount of deionized water equivalent to the 50% of the final volume of the composition, at a temperature of about 70° C. to about 85° C. and under agitation;
   b) cooling down the solution 35° C. and adding the sorbitol and the sodium citrate while agitating up to the complete dissolution;
   c) adding the propylene glycol under agitation;
   d) adding the sodium ibandronate and agitating up to a complete dissolution.

12. The method of claim 11, further comprising, after step d), the step of bringing the pH of the solution to about 6.5 to about 7.

13. A method of making the composition of claim 1, comprising the following steps:
   a) dissolving the pH regulating agent in deionized water to form a solution;
   b) adding the ibandronate to the solution of step a) and agitating the solution until obtaining a complete dissolution;
   c) adding the co-solvent while maintaining said agitation;
   d) adding deionized water for bringing the solution to a final weight and sterilizing the solution by passing it through 0.22 μm filter.

14. The method of claim 13, further comprising, before step d), the step of measuring the pH of the solution and bringing the pH to about 2 to about 3.

15. A method of treating a bone disease in a patient in need thereof, the method comprising administering to the patient about 2.5 mg/day to about 10 mg/day of ibandronaic acid or salts thereof in the composition of claim 1.

16. The method of claim 15, wherein the administration of the composition is selected from the group comprising via sublingual and via intranasal.

* * * * *